(12) United States Patent
Burvenich et al.

(10) Patent No.: US 7,288,377 B2
(45) Date of Patent: Oct. 30, 2007

(54) ADH1C

(75) Inventors: Silvia Burvenich, Washington, DC (US); Andrea Carmine, Bromma (SE); Dagmar Galter, Bromma (SE); Lars Olson, Lidingo (SE); Olof Sydow, Stockholm (SE)

(73) Assignee: AstraZeneca AB, Sodertalje (SE)

( * ) Notice: Subject to any disclaimer, the term of this patent is extended or adjusted under 35 U.S.C. 154(b) by 504 days.

(21) Appl. No.: 10/776,211

(22) Filed: Feb. 12, 2004

(65) Prior Publication Data

US 2004/0214213 A1   Oct. 28, 2004

Related U.S. Application Data

(60) Provisional application No. 60/462,704, filed on Apr. 15, 2003.

(51) Int. Cl.
*C12Q 1/68* (2006.01)
*C12P 19/34* (2006.01)

(52) U.S. Cl. .......................................... 435/6; 435/91.1

(58) Field of Classification Search .................... None
See application file for complete search history.

(56) References Cited

OTHER PUBLICATIONS

Buervenich et al. A rare truncating mutation in ADH1C (G78Stop) shows significant association with Parkinson's disease in a large international sample. Arch. Neurol. (2005) 62(1): 74-78.*
Schmitt et al. The ADH1C stop mutation in multiple system atrophy patients and health probands in the United Kingdom and Germany. Mov. Disorders (2006) available online in advance of print on Sep. 7, 2006, pp. 1-2.*
Buervenich et al. Alcohol dehydrogenase alleles in Parkinson's disease. Mov. Disorders (2000) 15: 813-818.*
Tan et al. Alcohol dehydrogenase polymorphism and Parkinson's disease. Neuroscience Lett. (2001) 305: 70-72.*

* cited by examiner

*Primary Examiner*—Jeffrey Fredman
*Assistant Examiner*—David C. Thomas
(74) *Attorney, Agent, or Firm*—Young & Thompson

(57) ABSTRACT

The present invention relates to a method for identifying individuals with Parkinson's disease and/or individuals at risk for developing Parkinson's disease, comprising screening nucleic acids from the individual for a mutation in the ADH1C gene, as well as different uses thereof.

5 Claims, 8 Drawing Sheets

```
   1 atgcactcaa gcagagaaga aatccacaag tactcaccag cctcctggtc tgcagagaag
  61 acagaatcaa tatg agc aca gca gga aaa gta atc aaa tgc aaa gca gct gtg cta tgg g
                   M   S   T   A   G   K   V   I   K   C   K   A   A   V   L   W   E    17
 121 ag tta aag aaa ccc ttt tcc att gag gag gta gag gtt gca cct cct aag gct cat gaa g
        L   K   K   P   F   S   I   E   E   V   E   V   A   P   P   K   A   H   E   V  37
 181 tt cgc att aag atg gtg gct gca gga atc tgt cgt tca gat gag cat gtg gtt agt ggc a
        R   I   K   M   V   A   A   G   I   C   R   S   D   E   H   V   V   S   G   N  57
 241 ac ctg gtg acc ccc ctt cct gtg att tta ggc cat gag gca gcc ggc atc gtg gaa agt g
        L   V   T   P   L   P   V   I   L   G   H   E   A   A   G   I   V   E   S   V  77
 301 tt gga gaa ggg gtg act aca gtc aaa cca ggt gat aaa gtc atc ccg ctc ttt act cct c
        G   E   G   V   T   T   V   K   P   G   D   K   V   I   P   L   F   T   P   Q  97
 361 ag tgt gga aaa tgc aga att tgt aaa aac cca gaa agc aac tac tgc ttg aaa aat gat c
        C   G   K   C   R   I   C   K   N   P   E   S   N   Y   C   L   K   N   D   L 117
 421 ta ggc aat cct cgg ggg acc ctg cag gat ggc acc agc agg ttc acc tgc agc ggg aag c
        G   N   P   R   G   T   L   Q   D   G   T   R   R   F   T   C   S   G   K   P 137
 481 cc atc cac cac ttc gtc ggc gtc agc acc ttc tcc cag tac aca gtg gtg gat gag aat g
        I   H   H   F   V   G   V   S   T   F   S   Q   Y   T   V   V   D   E   N   A 157
 541 ca gtg gcc aaa att gat gca gcc tcg ccc ctg gag aaa gtc tgc ctc att ggc tgt gga t
        V   A   K   I   D   A   A   S   P   L   E   K   V   C   L   I   G   C   G   F 177
 601 tt tcg act ggt tat ggg tct gca gtc aaa gtt gcc aag gtc acc cca ggg tct acc tgt g
        S   T   G   Y   G   S   A   V   K   V   A   K   V   T   P   G   S   T   C   A 197
 661 ct gtg ttt ggc ctg gga ggg gtc ggc cta tct gtt gtt atg ggc tgt aaa gca gct gga g
        V   F   G   L   G   G   V   G   L   S   V   V   M   G   C   K   A   A   G   A 217
 721 ca gcc aga atc att gct gtg gac atc aac aag gac aaa ttt gca aag gct aaa gag ttg g
        A   R   I   I   A   V   D   I   N   K   D   K   F   A   K   A   K   E   L   G 237
 781 gg gcc act gaa tgc atc aac cct caa gac tac aag aaa ccc att cag gaa gtg cta aag g
        A   T   E   C   I   N   P   Q   D   Y   K   K   P   I   Q   E   V   L   K   E 257
 841 aa atg act gat gga ggt gtg gat ttt tcg ttt gaa gtc atc ggt cgg ctt gac acc atg a
        M   T   D   G   G   V   D   F   S   F   E   V   I   G   R   L   D   T   M   M 277
 901 tg gct tcc ctg tta tgt tgt cat gag gca tgt ggc aca agt gtc att gta ggg gta cct c
        A   S   L   L   C   C   H   E   A   C   G   T   S   V   I   V   G   V   P   P 297
 961 ct gat tcc cag aac ctc tca ata aac cct atg ctg cta ctg act gga cgc acg tgg aaa g
        D   S   Q   N   L   S   I   N   P   M   L   L   L   T   G   R   T   W   K   G 317
1021 ga gct att ttt gga ggc ttt aag agt aaa gaa tct gtc ccg aaa ctt gtg gct gac ttt a
        A   I   F   G   G   F   K   S   K   E   S   V   P   K   L   V   A   D   F   M 337
1081 tg gct aag aag ttt tca ctg gat gca tta ata aca aat att tta cct ttt gaa aaa ata a
        A   K   K   F   S   L   D   A   L   I   T   N   I   L   P   F   E   K   I   N 357
1141 at gaa gga ttt gac ctg ctt cgc tct gga aag agt atc cgt acc gtc ctg acg ttt tgaa
        E   G   F   D   L   L   R   S   G   K   S   I   R   T   V   L   T   F   STOP 375
1201 acaatacaga tgccttccct tgtagcagtt ttcagcctcc tctaccctac atgatctgga
1261 gcaacagcta ggaaatatca ttaattctgc tcttcagaga tgttaaaaat aaattacacg
1321 tgggagcttt ccaaagaaat ggaaattgat gggaaattat tgtcaagca aatgtttaaa
```

```
1381 atccaaatga gaactaaata aagtgttgaa catcaactgg ggaattgaag ccaataaacc
1441 ttccttctta accattcaaa aaaaaaaaaa
```

Figure 1

| Number | forward sequences |
|---|---|
| F1 | TGAGAAGGGGTGAC |
| F2 | CGTGGAAAGTGTTTG |
| F3 | TTTGAGAAGGGGTG |
| F4 | TTGAGAAGGGGTGA |
| F5 | GTGGAAAGTGTTTGAG |
| F6 | GTTTGAGAAGGGGT |
| F7 | TCGTGGAAAGTGTTT |
| F8 | AAAGTGTTTGAGAAGG |
| F9 | GAAAGTGTTTGAGAAGG |
| F10 | GGAAAGTGTTTGAGAA |
| F11 | TGTTTGAGAAGGGG |
| F12 | GTGTTTGAGAAGGGG |
| F13 | AAGTGTTTGAGAAGGG |
| F14 | AGTGTTTGAGAAGGG |
| F15 | TGGAAAGTGTTTGAGA |
| F16 | TTTGAGAAGGGGTGACTAC |
| F17 | TGAGAAGGGGTGACTACA |
| F18 | TTGAGAAGGGGTGACTACA |
| F19 | ATCGTGGAAAGTGTTTGA |
| F20 | GTTTGAGAAGGGGTGACT |
| F21 | CATCGTGGAAAGTGTTTG |
| F22 | GTGTTTGAGAAGGGGTG |
| F23 | AGTGTTTGAGAAGGGGTG |
| F24 | TGTTTGAGAAGGGGTGA |
| F25 | TCGTGGAAAGTGTTTGAG |
| F26 | AAGTGTTTGAGAAGGGGT |
| F27 | GTGGAAAGTGTTTGAGAAGG |
| F28 | TGGAAAGTGTTTGAGAAGG |
| F29 | GAAAGTGTTTGAGAAGGGG |
| F30 | AAAGTGTTTGAGAAGGGG |
| F31 | GCATCGTGGAAAGTGTT |
| F32 | GGAAAGTGTTTGAGAAGGG |
| F33 | CGTGGAAAGTGTTTGAGA |
| F34 | AGTGTTTGAGAAGGGGTGACTACA |
| F35 | TGTTTGAGAAGGGGTGACTACAGT |
| F36 | GAAAGTGTTTGAGAAGGGGTGAC |
| F37 | GGCATCGTGGAAAGTGTTTG |
| F38 | GGAAAGTGTTTGAGAAGGGGTG |
| F39 | TCGTGGAAAGTGTTTGAGAAGG |
| F40 | ATCGTGGAAAGTGTTTGAGAAGG |
| F41 | TGGAAAGTGTTTGAGAAGGGG |
| F42 | GTGGAAAGTGTTTGAGAAGGGG |
| F43 | GTGTTTGAGAAGGGGTGACTACAG |
| F44 | AGTGTTTGAGAAGGGGTGACTACAGTC |
| F45 | GTGTTTGAGAAGGGGTGACTACAGTC |
| F46 | AAAGTGTTTGAGAAGGGGTGACTACA |
| F17 | GAAAGTGTTTGAGAAGGGGTGACTACA |
| F30 | TTGAGAAGGGGTGACTACAGTCAAA |
| F39 | GGCATCGTGGAAAGTGTTTGA |
| F47 | TGGAAAGTGTTTGAGAAGGGGTG |
| F48 | GTGGAAAGTGTTTGAGAAGGGGTG |
| F49 | GGAAAGTGTTTGAGAAGGGGTGA |
| F50 | CGGCATCGTGGAAAGTGTTT |
| F51 | CATCGTGGAAAGTGTTTGAGAAGG |
| F52 | GCATCGTGGAAAGTGTTTGAGAA |
| F53 | ATCGTGGAAAGTGTTTGAGAAGGG |
| F54 | CGTGGAAAGTGTTTGAGAAGGG |
| F55 | AAGTGTTTGAGAAGGGGTGACTACAG | cont.

| | |
|---|---|
| F56 | GCCATGAGGCAGCCGGCATCG |
| F57 | GAGGCAGCCGGCATCGTGGAA |
| F58 | ATGAGGCAGCCGGCATCGTGGA |
| F59 | CCATGAGGCAGCCGGCATCGTG |
| F60 | ATCGTGGAAAGTGTTTGAGAAGGGGTGACTACAGTC |
| F61 | CGTGGAAAGTGTTTGAGAAGGGGTGACTACAGTC |
| F62 | GGCCATGAGGCAGCCGGCA |
| F63 | AGGCCATGAGGCAGCCGGCA |
| F64 | TAGGCCATGAGGCAGCCGGCA |
| F65 | TTAGGCCATGAGGCAGCCGGCA |
| F66 | TTTAGGCCATGAGGCAGCCGGCA |
| F67 | ATTTTAGGCCATGAGGCAGCCGGCA |
| F68 | TTTTAGGCCATGAGGCAGCCGGCA |
| F69 | CATGAGGCAGCCGGCATCGTGG |
| F70 | GGAAAGTGTTTGAGAAGGGGTGACTACAGTCAAACC |
| F71 | TGGAAAGTGTTTGAGAAGGGGTGACTACAGTCAAACC |
| F72 | TGAGGCAGCCGGCATCGTGG |
| F73 | CATCGTGGAAAGTGTTTGAGAAGGGGTGACTACA |
| F74 | GAGAAGGGGTGACTACAGTCAAACCAGGTACAGGA |
| F75 | GATTTTAGGCCATGAGGCAGCCGGC |
| F76 | GGGTGACTACAGTCAAACCAGGTACAGGATTCACA |
| F77 | GTGATTTTAGGCCATGAGGCAGCCGG |
| F78 | TGATTTTAGGCCATGAGGCAGCCGG |
| F79 | CCTGTGATTTTAGGCCATGAGGCAGCCG |
| F80 | CTGTGATTTTAGGCCATGAGGCAGCC |
| F81 | TGTGATTTTAGGCCATGAGGCAGCCG |
| F82 | TCGTGGAAAGTGTTTGAGAAGGGGTGACTACAGT |
| F83 | TGTTTGAGAAGGGGTGACTACAGTCAAACCAGGT |
| F84 | TTTGAGAAGGGGTGACTACAGTCAAACCAGGTACAGG |
| F85 | TTGAGAAGGGGTGACTACAGTCAAACCAGGTACAGG |
| F86 | TGAGAAGGGGTGACTACAGTCAAACCAGGTACAGG |
| F87 | GTTTGAGAAGGGGTGACTACAGTCAAACCAGGTACAG |
| F88 | GAAAGTGTTTGAGAAGGGGTGACTACAGTCAAACCAG |
| F89 | AGAAGGGGTGACTACAGTCAAACCAGGTACAGGATTC |
| F90 | GAAGGGGTGACTACAGTCAAACCAGGTACAGGATTC |
| F91 | GGGGTGACTACAGTCAAACCAGGTACAGGATTCA |
| F92 | AGGGGTGACTACAGTCAAACCAGGTACAGGATTCA |
| F93 | AAGGGGTGACTACAGTCAAACCAGGTACAGGATTCA |
| F94 | CCCTTCCTGTGATTTTAGGCCATGAGGCA |
| F95 | CAGCCGGCATCGTGGAAAGTGTTTG |
| F96 | GCATCGTGGAAAGTGTTTGAGAAGGGGTG |
| F97 | AAAGTGTTTGAGAAGGGGTGACTACAGTCAAACCAGG |
| F98 | AAGTGTTTGAGAAGGGGTGACTACAGTCAAACCAGG |
| F99 | AGTGTTTGAGAAGGGGTGACTACAGTCAAACCAGG |
| F100 | GTGTTTGAGAAGGGGTGACTACAGTCAAACCAGG |
| F101 | CAGTCAAACCAGGTACAGGATTCACACTCAGGG |
| F102 | GACTACAGTCAAACCAGGTACAGGATTCACACTCAGGG |
| F103 | ACAGTCAAACCAGGTACAGGATTCACACTCAGGG |
| F104 | TACAGTCAAACCAGGTACAGGATTCACACTCAGGG |
| F105 | CTACAGTCAAACCAGGTACAGGATTCACACTCAGGG |
| F106 | ACTACAGTCAAACCAGGTACAGGATTCACACTCAGGG |
| F107 | GGCAGCCGGCATCGTGGAAAGTG |
| F108 | AGGCAGCCGGCATCGTGGAAAGTG |
| F109 | GTGACTACAGTCAAACCAGGTACAGGATTCACACTCAGG |
| F110 | TGACTACAGTCAAACCAGGTACAGGATTCACACTCAGG |
| F111 | GGTGACTACAGTCAAACCAGGTACAGGATTCACACTCA |
| F112 | TCCTGTGATTTTAGGCCATGAGGCAGCC |
| F113 | TTCCTGTGATTTTAGGCCATGAGGCAGCC |
| F114 | CTTCCTGTGATTTTAGGCCATGAGGCAGCC |
| F115 | CCGGCATCGTGGAAAGTGTTTGAGAAGG |
| F116 | GGCATCGTGGAAAGTGTTTGAGAAGGGG | cont.

| | |
|---|---|
| F117 | CCTTCCTGTGATTTTAGGCCATGAGGCAGC |
| F118 | GCAGCCGGCATCGTGGAAAGTGTT |
| F119 | CGGCATCGTGGAAAGTGTTTGAGAAGGG |
| F120 | AGCCGGCATCGTGGAAAGTGTTTGAGA |
| F121 | GCCGGCATCGTGGAAAGTGTTTGAGA |

Number reverse sequences

| | |
|---|---|
| R1 | AACACTTTCCACGAT |
| R2 | AAACACTTTCCACGA |
| R3 | CAAACACTTTCCACG |
| R4 | CCTCATGGCCTAA |
| R5 | CCTCATGGCCTAAA |
| R6 | CCCCTTCTCAAACAC |
| R7 | CCCTTCTCAAACACT |
| R8 | CCCCTTCTCAAACA |
| R9 | TTCTCAAACACTTTCC |
| R10 | TCACCCCTTCTCAA |
| R11 | CCCTTCTCAAACACTT |
| R12 | GTCACCCCTTCTCA |
| R13 | CACCCCTTCTCAAA |
| R14 | ACCCCTTCTCAAAC |
| R15 | CTCAAACACTTTCCACGA |
| R16 | TCAAACACTTTCCACGAT |
| R17 | AACACTTTCCACGATGC |
| R18 | TCTCAAACACTTTCCACG |
| R19 | CAAACACTTTCCACGATG |
| R20 | CCCCTTCTCAAACACTTTC |
| R21 | CACCCCTTCTCAAACAC |
| R22 | CACCCCTTCTCAAACACT |
| R23 | CCTTCTCAAACACTTTCCAC |
| R24 | CCTTCTCAAACACTTTCCA |
| R25 | TCACCCCTTCTCAAACA |
| R26 | CCCTTCTCAAACACTTTCC |
| R27 | TGTAGTCACCCCTTCTCAA |
| R28 | ACCCCTTCTCAAACACTT |
| R29 | TGTAGTCACCCCTTCTCA |
| R30 | GTAGTCACCCCTTCTCAAA |
| R31 | CCCCTTCTCAAACACTTT |
| R32 | AGTCACCCCTTCTCAAAC |
| R33 | CAAACACTTTCCACGATGCC |
| R34 | CCTTCTCAAACACTTTCCACGA |
| R35 | CCTTCTCAAACACTTTCCACGAT |
| R36 | GTCACCCCTTCTCAAACACTTTC |
| R37 | CTGTAGTCACCCCTTCTCAAACAC |
| R38 | TGTAGTCACCCCTTCTCAAACACT |
| R39 | CCCCTTCTCAAACACTTTCCAC |
| R40 | CCCCTTCTCAAACACTTTCCA |
| R41 | ACTGTAGTCACCCCTTCTCAAACA |
| R42 | CACCCCTTCTCAAACACTTTCC |
| R43 | AAACACTTTCCACGATGCCG |
| R44 | 4TCAAACACTTTCCACGATGCC |
| R45 | CCCTTCTCAAACACTTTCCACGAT |
| R46 | CCCTTCTCAAACACTTTCCACGA |
| R47 | TTCTCAAACACTTTCCACGATGC |
| R48 | CCCTTCTCAAACACTTTCCACG |
| R49 | CCTTCTCAAACACTTTCCACGATG |
| R50 | TGTAGTCACCCCTTCTCAAACACTTTC |
| R51 | GACTGTAGTCACCCCTTCTCAAACAC |
| R52 | CACCCCTTCTCAAACACTTTCCAC |
| R53 | CACCCCTTCTCAAACACTTTCCA |
| R54 | TGACTGTAGTCACCCCTTCTCAAACA | cont.

| | |
|---|---|
| R55 | TCACCCCTTCTCAAACACTTTCC |
| R56 | CTGTAGTCACCCCTTCTCAAACACTT |
| R57 | GGTTTGACTGTAGTCACCCCTTCTCA |
| R58 | TTGACTGTAGTCACCCCTTCTCAAA |
| R59 | TGTAGTCACCCCTTCTCAAACACTTT |
| R60 | TTGACTGTAGTCACCCCTTCTCAAAC |
| R61 | CCCTTCTCAAACACTTTCCACGATGCCG |
| R62 | CCTTCTCAAACACTTTCCACGATGCCGG |
| R63 | TCTCAAACACTTTCCACGATGCCGGC |
| R64 | CCCCTTCTCAAACACTTTCCACGATGCC |
| R65 | GACTGTAGTCACCCCTTCTCAAACACTTTCCACGAT |
| R66 | ACTGTAGTCACCCCTTCTCAAACACTTTCCACGA |
| R67 | CACCCCTTCTCAAACACTTTCCACGATGC |
| R68 | GACTGTAGTCACCCCTTCTCAAACACTTTCCACG |
| R69 | TCTCAAACACTTTCCACGATGCCGGCT |
| R70 | TGTAGTCACCCCTTCTCAAACACTTTCCACGATG |
| R71 | CAAACACTTTCCACGATGCCGGCTG |
| R72 | CTGGTTTGACTGTAGTCACCCCTTCTCAAACACTTTC |
| R73 | CCTGGTTTGACTGTAGTCACCCCTTCTCAAACAC |
| R74 | CCTGGTTTGACTGTAGTCACCCCTTCTCAAACACT |
| R75 | GTTTGACTGTAGTCACCCCTTCTCAAACACTTTCCAC |
| R76 | GGTTTGACTGTAGTCACCCCTTCTCAAACACTTTCCA |
| R77 | ACCTGGTTTGACTGTAGTCACCCCTTCTCAAACA |
| R78 | GGTTTGACTGTAGTCACCCCTTCTCAAACACTTTCC |
| R79 | CCTGGTTTGACTGTAGTCACCCCTTCTCAAACACTT |
| R80 | CCTGGTTTGACTGTAGTCACCCCTTCTCAAACACTTT |

Figure 2

| Number | forward sequences |
|---|---|
| F1 | GAAGACAGTGTTCAGCTAACACTAACG |
| F2 | ACCTTGTGCAAGTCCTTTCGTC |
| F3 | CCTTGTGCAAGTCCTTTCGTC |
| F4 | GGTTGAAGGGTAGAATACACGCA |
| F5 | ACAGTGTTCAGCTAACACTAACGTGG |
| F6 | GACAGTGTTCAGCTAACACTAACGTG |
| F7 | AGACAGTGTTCAGCTAACACTAACGTG |
| F8 | CAGTGTTCAGCTAACACTAACGTGG |
| F9 | TAATGGTTGAAGGGTAGAATACACGC |
| F10 | ATAATGGTTGAAGGGTAGAATACACGC |
| F11 | TGGTTGAAGGGTAGAATACACGC |
| F12 | ATGGTTGAAGGGTAGAATACACGC |
| F13 | AATGGTTGAAGGGTAGAATACACGC |
| F14 | CCTTTCGTCTTTCATTGCCTCG |
| F15 | CTTTCGTCTTTCATTGCCTCG |
| F16 | TTTCGTCTTTCATTGCCTCG |
| F17 | CATAATGGTTGAAGGGTAGAATACACG |
| F18 | TGAAGGGTAGAATACACGCATGC |
| F19 | TGTGCAAGTCCTTTCGTCTTTC |
| F20 | GTCTTTCATTGCCTCGGTTTCC |
| F21 | TCTTTCATTGCCTCGGTTTCC |
| F22 | CTTTCATTGCCTCGGTTTCC |
| F23 | GACCTTGTGCAAGTCCTTTCG |
| F24 | TGACCTTGTGCAAGTCCTTTCG |
| F25 | GTGACCTTGTGCAAGTCCTTTCG |
| F26 | TTCAGCTAACACTAACGTGGAAGTTAC |
| F27 | CTTGTGCAAGTCCTTTCGTCTTT |
| F28 | TTGTGCAAGTCCTTTCGTCTTT |
| F29 | TTCCTCATCCAGGCTGACTAATC |
| F30 | TTGAAGGGTAGAATACACGCATG |
| F31 | GTTGAAGGGTAGAATACACGCATG |
| F32 | AGTGTTCAGCTAACACTAACGTGGA |
| F33 | AACCTAGTGCCTGGCATCTAGTAGTAC |
| F34 | CTAACCTAGTGCCTGGCATCTAGTAGT |
| F35 | GTGTTCAGCTAACACTAACGTGGAA |
| F36 | CCTAGTGCCTGGCATCTAGTAGTACA |
| F37 | ACCTAGTGCCTGGCATCTAGTAGTACA |
| F38 | TCTCCAGGCTCTAACCTAGTGCC |
| F39 | ATCTCCAGGCTCTAACCTAGTGCC |
| F40 | CTCCAGGCTCTAACCTAGTGCC |
| F41 | TATCTCCAGGCTCTAACCTAGTGCC |
| F42 | ATATCTCCAGGCTCTAACCTAGTGCC |
| F43 | TATATCTCCAGGCTCTAACCTAGTGCC |
| F44 | TGTTCAGCTAACACTAACGTGGAAG |
| F45 | CATGCCTGCCTGAAGTCATACA |
| F46 | CGTCTTTCATTGCCTCGGT |
| F47 | GCCTGCCTGAAGTCATACATGC |
| F48 | TCTAACCTAGTGCCTGGCATCTAGT |
| F49 | CATGTTCCCTGAGTGTGAATCC |
| F50 | CCTCATCCAGGCTGACTAATCTTG |

| Number | reverse complementary sequences |
|---|---|
| R1 | GGCTGCAGGAATCTGTCGTT |
| R2 | GCTGCAGGAATCTGTCGTTCA |
| R3 | TGGCTGCAGGAATCTGTCG |
| R4 | GGCTGCAGGAATCTGTCGT | cont.

| | |
|---|---|
| R5 | GGCTGCAGGAATCTGTCGTTC |
| R6 | GCTGCAGGAATCTGTCGTTCAG |
| R7 | CGTTCAGATGAGCATGTGGTTAGTG |
| R8 | CCTTCCTGTGATTTTAGGCCAT |
| R9 | TCAGATGAGCATGTGGTTAGTGG |
| R10 | GGGAAAAAGAGGAAGGTTTTAGACTG |
| R11 | CAACCTGGTGACCCCCCTT |
| R12 | CGTTCAGATGAGCATGTGGTTAG |
| R13 | CGTTCAGATGAGCATGTGGTTAGT |
| R14 | CCTTCCTGTGATTTTAGGCCA |
| R15 | AGATGAGCATGTGGTTAGTGGC |
| R16 | TTAGAAAATTGGGTTTGTTAAGTCCA |
| R17 | TGAGCATGTGGTTAGTGGCAAC |
| R18 | CCCTTCCTGTGATTTTAGGCC |
| R19 | GGGTTTGTTAAGTCCATCTGACAGTC |
| R20 | AAGAGTTCACAATCAATTTGCATTAGA |
| R21 | CAAGAGTTCACAATCAATTTGCATTA |
| R22 | AATCTGTCGTTCAGATGAGCATGT |
| R23 | AGGGAAAAGAGGAAGGTTTTAGACT |
| R24 | GAAAAGAGGAAGGTTTTAGACTGGAT |
| R25 | GGAAGGTTTTAGACTGGATAACCTTG |
| R26 | GCATGTGGTTAGTGGCAACCT |
| R27 | AGAAAATTGGGTTTGTTAAGTCCATC |
| R28 | GGGTTTGTTAAGTCCATCTGACAGT |
| R29 | CAAGGGAAAAGAGGAAGGTTTTAG |
| R30 | CCCCTTCCTGTGATTTTAGGC |
| R31 | CAAGAGTTCACAATCAATTTGCATTAG |
| R32 | TCAAGGGAAAAGAGGAAGGTTT |
| R33 | AAGGTTTTAGACTGGATAACCTTGGA |
| R34 | GGGATTATCAGCAAAACCCTTGA |
| R35 | TGGATAACCTTGGAGATAAACTGAATC |
| R36 | GGAAAAGAGGAAGGTTTTAGACTGG |
| R37 | TTGGGAATAGTAGGGATTATCAGCA |
| R38 | TGTGATTTTAGGCCATGAGGC |
| R39 | GGGATTATCAGCAAAACCCTTG |
| R40 | TGAGCATGTGGTTAGTGGCA |
| R41 | GGTGGCTGCAGGAATCTGTC |
| R42 | TCGTTCAGATGAGCATGTGGTTA |
| R43 | GGAATCTGTCGTTCAGATGAGC |
| R44 | TTTTCTTGGTGTTAATTTGCAATTTC |
| R45 | GGTGGCTGCAGGAATCTGT |
| R46 | AAGGGAAAAGAGGAAGGTTTTAGAC |
| R47 | GACTGGATAACCTTGGAGATAAACTGA |
| R48 | GAAGGTTTTAGACTGGATAACCTTGG |
| R49 | TGTGGTTAGTGGCAACCTGGT |
| R50 | TGGGTTTGTTAAGTCCATCTGACAG |

Figure 3

ADH1C

The present invention refers to a new method for identifying individuals at risk for Parkinson's disease, based on a mutation in the ADH1C gene, as well as to different uses thereof.

BACKGROUND

Parkinson's disease is a neurodegenerative disease that strikes men and women alike. It is estimated that it affects about 15 out of 10,000 individuals and usually it first appears at an age of about 55-60 years. Despite considerable efforts, the reason for the symptom-causing degeneration of the midbrain dopamine neurons in patients afflicted by this crippling, non-curable disorder is not known. Moreover, while many of the symptoms of Parkinson's disease can be mimicked by lesions or neurotoxin administration to experimental animals, the disease itself is not known in any other species than man, thus hampering research aimed at understanding the etiology and the development of new therapies.

Exposure to toxic compounds in the environment remains one hypothetical cause of the disease although epidemiological studies have generated few clues as to its etiology. More recently, an interest in familial forms of the disease has indicated the presence of genetic components and linkage to an area on chromosome 4 has been reported and is discussed in more detail below.

Thus, in recent linkage studies, autosomal dominant or autosomal recessive types of Parkinson's disease have been mapped to several different loci in the human genome. Although these types of Parkinson's disease often differ from sporadic Parkinson's disease and constitute only a small fraction of the total patient population, the reported loci might confer susceptibility also for idiopatic forms of Parkinson's disease.

Polymeropoulos et al. (Science 274, p. 1197 (1996)) mapped autosomal dominant Parkinson to chromosome 4q21-q23. They called this area "PARK1". Later, they found a mutation in the gene for alpha-synuclein which segregated with the disease in one large Italian and three Greek kindreds and which they could not find in healthy control individuals. A mutation in the α-synuclein gene was identified in the families with Parkinson's disease (Polymeropoulos et al., Science 276, p. 2045-2047 (1997)). However, in spite of large efforts by other groups to find synuclein mutations in their own patients, they failed to identify any mutations in the alpha-synuclein gene in their material.

Interestingly, Vaughan et al. (Hum. Mol. Genet. 7, 751 (1998)) have reported one German family with autosomal dominant Parkinsonian to show linkage to the PARK1 region 4q21-q23. In this family, no mutations in alpha-synuclein could be identified. Said authors suggest that there might be another gene in the same locus that might account for the disease. In this case, the synuclein mutation in the Italian and Greek kindreds may be a marker that segregates with the "true" disease gene.

In WO 00/00621 the human gene encoding alcohol dehydrogenase 7 (ADH7) was shown to be associated with the development of Parkinson's disease and Parkinson related mutations (M1-M7) in the wildtype ADH7 gene were identified.

Alcohol dehydrogenases (ADH) are zinc metalloenzymes that oxidize alcohols to aldehydes or ketones. In addition to ethanol these enzymes also make important modifications to retinol, steroids, and fatty acids. The mammalian ADH system is divided into six classes, ADH1-ADH6, whereof five have been identified in man. ADH1C (formerly known as ADH3) is located within a cluster of alcoholdehydrogenases on human chromosome 4q21-q23. ADH1C is involved in retinoic acid synthesis from retinal. Since retinoic acid is likely to be of importance for dopamine neuron development and maintenance, genetic disturbances in these enzymes may render dopamine neurons of carriers more susceptible to stressors and may thus enhance the deleterious effects of environmental toxins.

Parkinson's disease is complex and the causes of the disease are multiple. Genetic mutations in alcohol or aldehyde dehydrogenases may constitute heritable risk factors for Parkinson's disease and can provide a link between endogenous metabolic pathways and the outside world (such as dietary retinal and toxic aldehydes). Thus, the more genetic mutations identified, the bigger the chance to develop a reliable diagnostic and prognostic tool for the disease.

Today there is no way of predicting or diagnosing Parkinson's disease prior to the onset of the symptoms. When symptoms occur, patients have typically already lost a very large number, in reality, the majority, of their dopamine nerve cells. Accordingly, a method for prediction and early diagnosis of Parkinson's disease would be very valuable.

DESCRIPTION OF THE FIGURES

FIG. 1 shows the cDNA and amino acid sequence of a human ADH1C indicating the site of nonsense mutation (gga—glycine becomes tga—STOP).

FIG. 2 shows oligonucleotides that can hybridize to the mutated site of ADH1C gene.

FIG. 3 shows oligonucleotides that bind to the ADH1C DNA sequence around the mutation. 'F'-primers bind in front of the mutation and 'R' primers behind the mutation

DEFINITIONS

In the present context, it is to be understood that the expression "Parkinson's disease" should be interpreted to include all kinds of parkinsonism, i.e. before the onset of the disease as well as early and late stages of the disease.

In this context the term "ADH1C" refers to class I alcohol dehydrogenase, gamma subunit. The three genes encoding alpha, beta and gamma subunits are tandemly organized in a genomic segment as a gene cluster. Alternative names that have been used for ADH1C in the literature and in public databases include 'ADH3', 'ADH gamma subunit', and 'aldehyde reductase'.

In this context the term "allelic variant" refers to an alternative form of a gene found at the same locus on homologous chromosomes.

In this context the term "mini gene" refers to a construct of a gene with parts of the sequence removed which still remains functional. Intronless minigenes are commonly used in gene expression systems, since only information from the exons is necessary for the production of functional protein.

In this context the term "functional homologues" refers to sequences sharing perhaps a lower structural homology with the disclosed sequence, but exhibiting homologous function in vivo, in either the healthy or the diseased organism, e.g. coding the same or highly similar proteins with similar cellular functions.

The term "nonsense mutation" as used herein refers to a mutation which generates one of the nonsense codons, resulting in premature termination of polypeptides synthesis during translation. An example of such a mutation is the G78stop mutation.

The term "antibodies" as used herein refers to all types of immunoglobulins, including IgG, IgM, IgA, IgD, and IgE. The antibodies may be monoclonal or polyclonal and may be of any species of origin, including (for example) mouse, rat, rabbit, horse, or human, or may be chimeric antibodies, and include antibody fragments such as, for example, Fab, F(ab')2, and Fv fragments, and the corresponding fragments obtained from antibodies other than IgG.

In this context the phrase "hybridisation under stringent conditions" refers to criteria regarding temperature and buffers well know to those skilled in the art.

DETAILED DESCRIPTION OF THE INVENTION

The present invention is based on the identification of a mutation in the ADH1C gene that may lead to new disease pathways in the most common idiopathic type of Parkinson's disease. In contrast to other identified mutations, ADH1C constitutes a clear link to "outside" factors, such as environmental toxins or alike. The early diagnosis which the present invention enables together with preventive measures will be most valuable and fill a need that has been felt for a long time by both physicians and patients. Diagnostic tools, such as assays, e.g. for screening of samples, or similar methods, wherein the nucleotides according to the present invention are used, also enable a subclassing of the disease with a prognostic value and will assist in the differential diagnosis towards a series of Parkinson-like diseases and so called Parkinson+ cases. Simple blood tests will suffice to this end.

The present invention is based on the identification of a mutated form of the human gene encoding alcohol dehydrogenase 1C (ADH1C) as a gene significant in association with Parkinson's disease in humans. A subset of patients suffering from Parkinson's disease exhibit one herein defined mutation, which thus triggers the disease. Additionally, the identified mutant gene is capable of passing on the disease to a later generation.

The present invention refers to a method for identifying a person with Parkinson's disease and/or a person at risk for developing Parkinson's disease, comprising screening nucleic acids from said person for a mutation in an ADH1C gene which encodes a protein chain, said mutation causing a truncation of the expressed protein chain. The ADH1C gene is preferably selected from the group consisting of a gene having a cDNA sequence of SEQ ID NO. 1 and other ADH1C genes comprising a thymidine at or corresponding to position 303 in SEQ ID NO. 1.

The nonsense mutation in ADH1C, was selected from SNP database (dbSNP) rs#283413 using the BLAST SNP tool. It encodes a putative nonsense mutation in ADH1C exon 3, leading to early (after 78 of 350 amino acid residues) truncation of the protein chain. Since neither the active site nor the co-factor binding site are included in the remaining protein chain, this mutation is likely to equal a heterozygous "knock-out" of ADH1C in the carrier individual.

The present invention provides a method of screening, i.e. diagnosing or prognosing, for Parkinson's disease in a subject. The method comprises detecting the presence or absence of truncated ADH1C protein or of DNA encoding a truncated form of ADH1C in the subject. The presence of such isoform or DNA indicates that the subject is afflicted with Parkinson's disease or at risk of developing Parkinson's disease. Suitable subjects include those which have not previously been diagnosed as afflicted with Parkinson's disease, those which have previously been determined to be at risk of developing Parkinson's disease, and those who have been initially diagnosed as being afflicted with Parkinson's disease where confirming information is desired. Thus, the present invention may be employed in detecting both familial Parkinson's disease (late onset and early onset) as well as sporadic Parkinson's disease. Many Parkinson's disease patients encountered in practice have no obvious family history and have been classified as sporadic. However, genetic factors in early--and late--onset of familial Parkinson's disease are well documented. Early-onset Parkinson's disease is the classification usually used if the disease is diagnosed to occur before the age of 50 in humans.

Observing whether or not the truncated form of ADH1C is present or absent in a subject enables one to observe or determine whether or not a subject is afflicted with or at increased risk of developing Parkinson's disease. Affliction with the disease is more likely if truncated ADH1C is present. A subject with truncated ADH1C is at increased risk of developing Parkinson's disease over subjects in which truncated ADH1C is absent. A subject who is "at increased risk of developing Parkinson's disease" is one who is predisposed to the disease, has genetic susceptibility for the disease or is more likely to develop the disease than subjects in which truncated ADH1C is absent. Subjects with one allele of truncated ADH1C are as much as fifteen times as likely to be affected by Parkinson's disease as subjects with no truncated allele.

It is preferred and contemplated that the methods described herein be used in conjunction with other clinical diagnostic information known or described in the art which are used in evaluation of subjects with Parkinson's disease or suspected to be at risk for developing such disease.

The established nomenclature system as well as phenotypes and genotypes for ADH, are described in, for example, Duester, G. et al., Biochem Pharmacol. 1999 Aug. 1;58(3): 389-95, and Osier, M. V. et al., Am J Hum Genet. 2002 July;71(1):84-99, which are incorporated herein by reference. ADH1C polymorphisms are well described and available from public databases (http://www.ncbi.nlm.nih.gov/SNP/).

It will be readily appreciated that the detecting steps described herein may be carried out directly or indirectly. Thus, for example, if the subject is found to carry two wildtype alleles of ADH1C then it is determined that the subject is neither homozygous nor heterozygous for the truncated variant of ADH1C. Other means of indirectly determining allelic type could be by measuring polymorphic markers that are linked to the mutated ADH1C allele, as has been demonstrated for the VNTR (variable number tandem repeats) and the ApoB alleles (Decorter et al., DNA & Cell Biology 9(6), 461-69 (1990)).

The step of detecting the presence or absence of truncated ADH1C protein DNA encoding such variant may be carried out either directly or indirectly by any suitable means. A variety of techniques are known to those skilled in the art. All generally involve the step of collecting a sample of biological material containing either DNA or ADH1C protein from the subject, and then detecting whether or not the subject possesses truncated ADH1C or DNA encoding such isoform from that sample. For example, the detecting step may be carried out by collecting an ADH1C protein sample from the subject (for example, from a liver biopsy, or any other tissue or fluid containing ADH1C), and then determining the presence or absence of a truncated ADH1C variant in the sample (e.g., by isoelectric focusing or immunoassay).

The isolation and characterization of ADH1C is described, for example, in Montavon et al., Anal Biochem. 1989 January;176(1):48-56, and Keung, W. M. et al. Anal Biochem. 1985 Nov. 15;151(1):92-6, all of which are incorporated herein by reference. Isoelectric focusing is an electrophoretic technique by which the molecules are separated based on their isoelectric points (pI) along a continuous pH gradient. Reference proteins, commercially available (e.g., Sigma Chemical Company, St. Louis, Mo.), are used to indicate a gradient along which the sample proteins match up according to where their pH matches their pI.

The detecting step may be carried out by collecting a biological sample containing DNA from the subject, and then determining the presence or absence of DNA encoding a truncated ADH1C protein in the biological sample. Any biological sample which contains the DNA of that subject may be employed, including tissue samples and blood samples, with blood cells being a particularly preferred source. The determination can be made on amplified or non-amplified DNA. The amino acid sequences and nucleic acid sequences for ADH1C are known and described. For the nucleic acid sequence of ADH1C, see for example Yasunami et al., Genomics 1990 June;7(2):152-8, and Ikuta, T. et al., Proc Natl Acad Sci USA 1986 February;83(3):634-8, all incorporated herein by reference; and for the amino acid sequence information, see for example Yokoyama S. and Yokoyama R., Mol Biol Evol 1987 September;4(5):504-13.

Determining the presence or absence of DNA encoding truncated ADH1C may be carried out with an oligonucleotide probe labelled with a suitable detectable group, or by means of an amplification reaction such as a polymerase chain reaction or ligase chain reaction (the product of which amplification reaction may then be detected with a labelled oligonucleotide probe or a number of other techniques). Further, the detecting step may include the step of detecting whether the subject is heterozygous or homozygous for the gene encoding truncated ADH1C. Numerous different oligonucleotide probe assay formats are known for a person skilled in the art.

Amplification of a selected, or targeted, nucleic acid sequence may be carried out by any suitable means. Examples of suitable amplification techniques include, but are not limited to, polymerase chain reaction, ligase chain reaction, strand displacement amplification (see G. Walker et al., Proc. Natl. Acad. Sci. USA 89, 392-396 (1992); G. Walker et al., Nucleic Acids Res. 20, 1691-1696 (1992)), transcription-based amplification (see D. Kwoh et al., Proc. Natl. Acad Sci. USA 86, 1173-1177 (1989)), self-sustained sequence replication (or "3SR") (see J. Guatelli et al., Proc. Natl. Acad. Sci. USA 87, 1874-1878 (1990)), the Q.beta. replicase system (see P. Lizardi et al., BioTechnology 6, 1197-1202 (1988)), nucleic acid sequence-based amplification (or "NASBA") (see R. Lewis, Genetic Engineering News 12 (9), 1 (1992)), the repair chain reaction (or "RCR") (see R. Lewis, supra), and boomerang DNA amplification (or "BDA") (see R. Lewis, supra). Polymerase chain reaction is currently preferred.

DNA amplification techniques such as the foregoing can involve the use of a probe, a pair of probes, or two pairs of probes which specifically bind to DNA encoding truncated ADH1C, but do not bind to DNA encoding wildtype ADH1C under the same hybridization conditions, and which serve as the primer or primers for the amplification of the mutated ADH1C DNA or a portion thereof in the amplification reaction. FIG. 1 shows a wildtype ADH1C cDNA and amino acid sequence.

In general, an oligonucleotide probe which is used to detect DNA encoding truncated ADH1C is an oligonucleotide probe which binds to DNA encoding truncated ADH1C, but does not bind to DNA encoding wildtype ADH1C under the same hybridization conditions. Examples of oligonucleotides that can hybridise to the mutation according to the invention can be seen in FIG. 2. The oligonucleotide probe is labelled with a suitable detectable group, such as those set forth below in the description of the use of antibodies. Accordingly, the invention also relates to a screening method comprising hybridising under stringent conditions an oligonucleotide to the ADH1C gene comprising the mutation.

When PCR conditions allow for amplification of wildtype as well as truncated ADH1C, the types can be distinguished by electrophoresis on denaturing gradient gels (DGGE), single-strand conformation polymorphism analysis (SSCP), heteroduplex analysis (HA), temperature gradient gel electrophoresis (TGGE), cleavage-fragment-length polymorphism analysis (CFLP), denaturing HPLC (dHPLC), chemical cleavage of mismatch (CCM), carbodiimide modification assay (CDI), enzymatic cleavage of mismatch (ECM), UNG-mediated T Scan, direct sequencing, DNA chip resequencing, Pyrosequencing™, allele-specific primer extension (GBA; TDI), oligonucleotide ligation assay (OLA; DOL), Taqman-ASO, restriction fragment length polymorphism analysis (RFLP), mass spectometry, the Invader™ assay or BeadArray™ technology. For further descriptions of these techniques, see Eric D. Green et al. (editors) "Genome Analysis" Vol. 1 (Analyzing DNA; 1997) and Vol. 4 (Mapping Genomes; 1999), Cold Spring Harbor Laboratory Press, USA; Fors, L. et al., Pharmacogenomics 2000, Vol. 1, pp. 219-229; Oliphant et al., supplement to Biotechniques, June 2002; for detailed description of detection of mutated ADH1C by Pyrosequencing™. For several of these techniques, prior amplification by PCR can be omitted when sufficiently large amounts of genomic DNA can be made available from each subject.

Examples of primers effective for amplification and identification of the wildtype as well as the mutated ADH1C gene by PCR followed by Pyrosequencing™ are described in the end of the present description. Oligonucleotides that bind to the ADH1C genomic sequence around the mutation for amplification purposes can be seen in FIG. 3. Alternatively, primers specific for the ADH1C mutation leading to the protein truncation could also be employed.

Amplification by PCR can be substituted by amplification by the ligase chain reaction (LCR) in accordance with known techniques. See, e.g., R. Weiss, Science 254, 1292 (1991). In general, the reaction is carried out with two pairs of oligonucleotide probes: one pair binds to one strand of the sequence to be detected; the other pair binds to the other strand of the sequence to be detected. Each pair together completely overlaps the strand to which it corresponds. The reaction is carried out by, first, denaturing (e.g., separating) the strands of the sequence to be detected, then reacting the strands with the two pairs of oligonucleotide probes in the presence of a heat stable ligase so that each pair of oligonucleotide probes is ligated together, then separating the reaction product, and then cyclically repeating the process until the sequence has been amplified to the desired degree. Detection of the product may then be carried out according to methods well known in the art.

As a further alternative to isoelectric focusing and techniques for allele detection, the step of determining the presence or absence of the truncated ADH1C variant in a sample may be carried out by an antibody assay with an antibody which selectively binds to truncated ADH1C (i.e., an antibody which binds to truncated ADH1C but exhibits essentially no binding to wildtype ADH1C in the same binding conditions).

According to another embodiment the invention relates to a method for screening for the mutation according to the invention, wherein the screening comprises restriction enzymes specifically recognizing a nucleotide sequence of the mutation or surrounding the mutation to be detected. Restrictions enzymes suitable for the invention will be apparent for a person skilled in the art.

Antibodies used to selectively or specifically bind truncated ADH1C can be produced by any suitable technique. For example, monoclonal antibodies may be produced in a hybridoma cell line according to the techniques of Kohler and Milstein, Nature 265, 495-97 (1975). Truncated ADH1C may be obtained from a human patient determined to be carrier therefore, then purified and used as the immunogen for the production of monoclonal or polyclonal antibodies. Purified truncated forms of ADH1C may be produced by recombinant means to express a biologically active isoform, or even an immunogenic fragment thereof may be used as an immunogen. Monoclonal Fab fragments may be produced in *Escherichia coli* from the known sequences by recombinant techniques known to those skilled in the art. See, e.g., W. Huse, Science 246, 1275-81 (1989) (recombinant Fab techniques); P. Wenham et al., Lancet 337, 1158 (1991) (ApoE PCR primers). The DNA encoding wildtype ADH1C can be obtained and converted to the mutated form by site-directed mutagenesis. See, e.g., T. Kunkel et al., Methods in Enzymol. 154, 367-382 (1987); T. Kunkel, U.S. Pat. No. 4,873, 192.

For this invention, an antibody selectively or specifically binding wildtype or truncated ADH1C (ligand) generally refers to a molecule capable of reacting with or otherwise recognizing or binding such a ligand. An antibody has binding affinity for a ligand or is specific for a ligand if the antibody binds or is capable of binding the ligand as measured or determined by standard antibody-antigen or ligand-receptor assays, for example, competitive assays, saturation assays, or standard immunoassays such as ELISA or RIA. This definition of specificity applies to single heavy and/or light chains, CDRs, fusion proteins or fragments of heavy and/or light chains, which are specific for the ligand if they bind the ligand alone or in combination.

Antibody assays (immunoassays) may, in general, be homogeneous assays or heterogeneous assays. In a homogeneous assay the immunological reaction usually involves the specific antibody, a labeled analyte, and the sample of interest. The signal arising from the label is modified, directly or indirectly, upon the binding of the antibody to the labeled analyte. Both the immunological reaction and detection of the extent thereof are carried out in a homogeneous solution. Immunochemical labels which may be employed include free radicals, radioisotopes, fluorescent dyes, enzymes, bacteriophages, coenzymes, and so forth.

In a heterogeneous assay approach, the reagents are usually the specimen, the antibody of the invention and a system or means for producing a detectable signal. Similar specimens as described above may be used. The antibody is generally immobilized on a support, such as a bead, plate or slide, and contacted with the specimen suspected of containing the antigen in a liquid phase. The support is then separated from the liquid phase and either the support phase or the liquid phase is examined for a detectable signal employing means for producing such signal. The signal is related to the presence of the analyte in the specimen. Means for producing a detectable signal include the use of radioactive labels, fluorescent labels, enzyme labels, and so forth. For example, if the antigen to be detected contains a second binding site, an antibody which binds to that site can be conjugated to a detectable group and added to the liquid phase reaction solution before the separation step. The presence of the detectable group on the solid support indicates the presence of the antigen in the test sample. Examples of suitable immunoassays are the radioimmunoassay, immunofluorescence methods, enzyme-linked immunoassays, and the like.

Those skilled in the art will be familiar with numerous specific immunoassay formats and variations thereof, which may be useful for carrying out the method disclosed herein. See E. Maggio, Enzyme-Immunoassay, (1980) (CRC Press, Inc., Boca Raton, Fla.); see also U.S. Pat. No. 4,727,022 to Skold et al. titled "Methods for Modulating Ligand-Receptor Interactions and their Application," U.S. Pat. No. 4,659, 678 to Forrest et al., U.S. Pat. No. 4,376,110 to David et al., U.S. Pat. No. 4,275,149 to Litman et al., U.S. Pat. No. 4,233,402 to Maggio et al., and U.S. Pat. No. 4,230,767 to Boguslaski et al.

Antibodies which selectively bind wildtype or truncated ADH1C may be conjugated to a solid support suitable for a diagnostic assay (e.g., beads, plates, slides or wells formed from materials such as latex or polystyrene) in accordance with known techniques, such as precipitation. Antibodies which bind wildtype or truncated ADH1C may likewise be conjugated to detectable groups such as radiolabels (e.g., $^{35}S$, $^{125}I$, $^{131}I$) enzyme labels (e.g., horseradish peroxidase, alkaline phosphatase), and fluorescent labels (e.g., fluorescein) in accordance with known techniques.

Another embodiment of the present invention is a kit for determining if a subject is or was afflicted with or is or was at increased risk of developing Parkinson's disease and will include at least one reagent specific for detecting for the presence or absence of truncated ADH1C and instructions for observing that the subject is or was afflicted with or is or was at increased risk of developing Parkinson's disease if the presence of truncated ADH1C is detected. The truncated ADH1C gene is selected from the group consisting of a gene of SEQ ID NO. 1 and other ADH1C genes comprising a thymidine at or corresponding to position 303 in SEQ ID NO. 1 The kit may optionally include one or more oligonucleotides of or similar to those shown in FIGS. 2 and 3 for detection of the truncated ADH1C gene or instructions for isoelectric focusing methods for detecting truncated ADH1C.

Preferably the kit of the present invention also comprises in sealed container(s) one or more restriction enzymes specifically recognizing a nucleotide sequence of the mutation or surrounding the mutation to be detected on the ADH1C gene.

Diagnostic kits for carrying out antibody assays may be produced in a number of ways. In one embodiment, the diagnostic kit comprises (a) an antibody which binds wildtype or truncated ADH1C protein conjugated to a solid support and (b) a second antibody which binds wildtype or truncated ADH1C conjugated to a detectable group. The reagents may also include ancillary agents such as buffering agents and protein stabilizing agents, e.g., polysaccharides and the like. The diagnostic kit may further include, where necessary, other members of the signal-producing system of which system the detectable group is a member (e.g., enzyme substrates), agents for reducing background interference in a test, control reagents, apparatus for conducting a test, and the like. A second embodiment of a test kit comprises (a) an antibody as above, and (b) a specific binding partner for the antibody conjugated to a detectable group. Ancillary agents as described above may likewise be included. The test kit may be packaged in any suitable manner, typically with all elements in a single container along with instructions for carrying out the test.

In addition, the invention also relates to the use of isolated human wildtype ADH1C, or any molecule which is capable of taking over a missing function of truncated ADH1C, or of compensating for a lack of ADH1C function or abolishing an ADH1C dysfunction, in the manufacture of a therapy or medicament for treating Parkinson's disease, preferably Parkinson's disease caused by the above defined mutation in the ADH1C gene.

In an alternative embodiment, the invention relates to the use of an alcohol or retinoid normally metabolized by ADH1C, or any alternative ADH1C substitute, such as an enzyme, in the manufacture of a therapy or medicament for treating Parkinson's disease, preferably Parkinson's disease caused by the above defined mutation in the ADH1C gene. Accordingly, the invention also relates to a pharmaceutical composition for treating and/or preventing Parkinson's disease caused by the herein described mutation in the ADH1C gene. The composition comprises wildtype ADH1C in a therapeutically effective dose and a pharmaceutically acceptable carrier, such as an aqueous carrier, e.g. buffered saline and the like, which is sterile and free of undesirable matter.

In an alternative embodiment of this aspect of the invention, the pharmaceutical composition comprises a substrate or a product of ADH1C, such as an alcohol or retinoid normally metabolized by ADH1C, or any alternative ADH1C substitute, such as an enzyme, in a therapeutically effective dose and a pharmaceutically acceptable carrier. Even though the use of retinoid compounds have been suggested before for the prevention and treatment of conditions and diseases associated with human papilloma virus (see U.S. Pat. No. 5,514,825), the present invention suggests for the first time such uses for the treatment or prevention of Parkinson's disease. The amounts effective of wildtype ADH1C as the active ingredient will depend upon the severity of the condition and the general state of the patient's health. A composition according to the invention may also comprise suitable excipients and auxiliary substances as required, pH-adjusting and buffering agents, toxicity adjusting agents, stabilizers, etc., such as conventionally used in the pharmaceutical industry. The present composition may be administered in a variety of unit dosage forms depending on the method of administration. For example, unit dosage forms suitable for oral administration include powder, tablets, pills, capsules and lozenges, the oral preparation being most preferred for reasons of simplicity. Actual methods for preparing parenterally administrable compositions are known or apparent to those skilled in the art and are described in more detail in such publications as Remington's Pharmaceutical Science, 15th ed., Mack Publishing Company, Easton, Pa. (1980).

The present invention also relates to all of the pharmaceutical aspects discussed above, wherein the previously disclosed peptides, polypeptides or proteins capable of binding a nucleotide comprising the sequence of the mutation leading to truncation of the ADH1C protein chain are used.

The pharmaceutical use of ADH1C according to the invention is based on the following proposed pathways.

1. Direct Involvement of ADH1C in Retinoid Metabolism

A retinoid-handling aldehyde dehydrogenase was recently shown to be specifically expressed in the midbrain dopamine neurons of the rat brain. To convert retinol to retinoic acid, one alcohol dehydrogenase and one aldehyde dehydrogenase are needed. The dopamine neurons also express the transcription factor Nurr1 and recent knock-out experiments demonstrate that this factor is required for the development of dopamine neurons as well as for proper function of dopamine neurons in postnatal adult life. Nurr1 may itself be activated by retinoid, which however remains to be proven. Importantly, Nurr1 forms heterodimers with RXR, which is activated by 9-cis retinoic acid. Thus, a mechanism is proposed, in which the dopamine neurons are critically dependent upon a specific combination of an aldehyde and an alcohol dehydrogenase (possibly ADH1C) needed to generate retinoids necessary to activate RXR-Nurr1 mediated transcriptional control of vital genes in these neurons.

2. ADH1C as a Detoxifying Enzyme in the Gastrointestinal Tract

ADH1C can also convert aldehydes into less aggressive alcohols and, to a lesser extent, into acids, thus protecting from the absorption of aldehydes in food, or generated during digestion. It is proposed that if ADH1C, which mainly resides in the liver in humans, is defect, then toxic aldehydes reach the circulation and pass the blood-brain barrier to damage dopamine neurons. Alternatively, such aldehydes lead to secondary effects, eventually damaging the dopamine neurons.

The present invention will provide a base for future development of novel therapies. Since ADH1C is proposed to be directly involved in the disease process, the now recognized mechanism of ADH1C according to the invention will form an important basis for the development of novel therapeutics and drugs. One such novel drug is a pharmaceutical preparation comprising one or more retinoid agonists together with a suitable pharmaceutically acceptable carrier. Another such drug is one that can handle toxic aldehydes and compensate for the lack of ADH1C. This may e.g. be in the form of a pill, that acts in the intestinal tract, or any other suitable form as discussed above.

In another embodiment the present invention also relates to a method of treating a patient by administering a drug that compensates for the lack of ADH1C, e.g. by administering a therapeutically effective dose of ADH1C.

The present invention also relates to animal models of Parkinson's disease. Such a model can be a transgenic, non-human animal, such as a rodent, comprising a human ADH1C gene selected from the group consisting of a gene of SEQ ID NO. 1 and other ADH1C genes comprising a thymidine at or corresponding to position 303 in SEQ ID NO. 1, said animal is used as a model in the development of prevention/treatment strategies for Parkinson's disease. In another embodiment the animal model comprises a human wildtype ADH1C gene selected from the group consisting of SEQ ID. NO. 2 or equivalent functional homologues thereof.

In another embodiment the invention relates to a transgenic non-human animal, such as a rodent, wherein an ADH1 gene encoding a protein chain comprises a mutation causing a truncation of the expressed protein chain. The mutation corresponds to the mutation causing the truncation of the protein encoded for by the ADH1C gene of SEQ ID NO. 1 or equivalent functional homologues thereof. The animal can be either homo- or heterozygous for the mutation.

As mentioned above, Parkinson's disease does not exist in animals, which hitherto has imposed a substantial problem in the research within this field. Research has therefore been based on models in which those neurons that die in the human disease are damaged mechanically or chemically in animals to generate similar symptoms. As the ADH1C mutation according to the invention can cause Parkinson's disease in human beings, the teaching according to the invention now for the first time enables the generation of "Parkinson mice" using gene targeting techniques.

For example, based on the present invention, the corresponding class I alcohol dehydrogenase gene in the mouse can be targeted by a classical knock-out strategy or more advanced transgenic techniques that simulate the effect of the human mutation in the carrier animal.

Accordingly, the present invention also relates to genetically manipulated animals, such as mice, that contain the mutation according to the invention.

In order to produce such an animal, a nucleotide according to the invention is introduced in a suitable vector by standard protocols. (For production of transgenic animals, such as mice, see U.S. Pat. No. 5,455,169 in the name of Mullen, and references cited therein.) Thus, in the animals according to the invention, the human genomic defect(s) can be precisely replicated, leading to animals that develop a disease with the human characteristics. Several different approaches can be taken, in which the human mutated gene can substitute for the mouse ADH class I gene, alternatively, the mouse class I alcohol dehydrogenase gene can be modified in a way that resembles the effect of the mutation in the human protein. The model animals according to the invention, preferably model mice, can be of great value to researchers and the pharmaceutical industry alike as tools for the development of new treatments and therapies, such as medicaments.

In another embodiment of the invention is a cell line comprising the ADH1C gene corresponding to SEQ ID. NO. 2, an allelic variant, minigene, or an equivalent functional homologue thereof to over-express ADH1C, an isoform of ADH1C or functional homologues thereof or at least a portion thereof. The invention also relates to a method for prevention and/or treatment of Parkinson's disease, wherein a pharmaceutical composition comprising cells of the above celline is administered in a therapeutically effective dose.

In another embodiment the cell line comprise the ADH1C gene corresponding to SEQ ID NO. 1 or other ADH1C genes comprising a thymidine at or corresponding to position 303 in SEQ ID NO. 1, an allelic variant, mini-gene, a homolog thereof to express a non-functional ADH1C or at least a portion thereof. The invention also relates to a method for prevention and/or treatment of Parkinson's disease, wherein a pharmaceutical composition comprising cells of the above cell line is administered in a therapeutically effective dose.

Another embodiment of the invention is a method for screening for pharmaceutical compounds, pharmaceutical compositions or nucleic acids that interfere with ADH1C expression or ADH1C-induced pathology, wherein the method comprise at least one of the cell lines defined above.

In a further aspect, the invention also relates to the use of the specific wildtype sequences that correspond to the site of the truncating mutation in gene therapy methods aimed at treating and/or preventing Parkinson's disease. Even though all of the wild type ADH1C gene has been published before, no existence and exact loctions of mutations that cause Parkinson's disease were known before the invention.

Accordingly, it was not possible to direct a therapy to any specific protein product of the ADH1C gene before the present invention.

In another aspect the invention relates to a recombinant vector comprising a wildtype ADH1C gene, allelic variant, minigene or a homolog thereof. More specific a recombinant vector comprising a cDNA of the ADH1C gene, a replication DNA fragment that provides for replication of said cDNA, a promoter DNA fragment that provides for transcription of the cDNA in a eukaryotic cell, and a translation DNA fragment that provides for translation in a eukaryotic cell of mRNA from said cDNA, said cDNA and DNA fragments being operatively linked so as to provide for expression of said cDNA when said vector is introduced into a eukaryotic cell. Accordingly the invention also relates to a cell comprising such a recombinant vector. The vector can be comprised in a viral or non-viral vector system mediating gene transfer in a non-human animal or in a human. In addition, the vector can be comprised in a recombinant cell mediating gene transfer in a non-human animal or in a human.

In yet another aspect the invention relates to a method for prevention and/or treatment of Parkinson's disease comprising a vector or a recombinant cell as defined above, which method comprises delivery of the vector or the recombinant cell to the patient.

The invention also encompasses nucleic acids (cDNA) for the transformation of cells in vitro and in vivo. These nucleic acids can then be inserted into any of a number of well known vectors for the transfection and transformation of target cells and organisms. The nucleic acids are transfected into cells, ex vivo or in vivo, through the interaction of the vector and the target cell. The ADH1C cDNA, under control of a suitable promoter, then expresses ADH1C and thereby mitigate the effects of the mutated or sick genes. For a review of gene therapy methods, see e.g. Anderson, Science (1992) 256: 808-813; Nabel and Felgner (1993) TIBTECH 11: 211-217; Mitani and Caskey (1993) TIBTECH 11: 162-166; Mulligan (1993) Science 926-932; Dillon (1993) TIBTECH 11: 167175; Miller (1992) Nature 357: 455-460; Van Brunt (1988) Biotechnology 6 (10): 1149-1154; Vigne (1995) Restorative Neurology and Neuroscience 8: 35-36; Kremer and Perricaudet (1995) British Medical Bulletin 51 (1) 31-44; Haddada et al. (1995) in Current Topics in Microbiology and Immunology, Doerfler and Bhm (eds) Springer-Verlag, Heidelberg Germany; and Yu et al., Gene Therapy (1994) 1: 13-26.

The invention will now be further described in the experimentals below, which are included herein for purposes of illustration only and are not intended to limiting to the invention.

EXPERIMENTAL

The methods we have used are just two ways of genotyping and we do not restrict ourselves to these detection methods. Other methods (existing or future developments) can be used for detection of the ADH1C nonsense mutation.

Background

The dramatic sequence change due to the nonsense mutation (G78stop mutation) in ADH1C was identified in three PD patients only in our Swedish material. One of the patients reported family history of disease (father and two brothers), while the other two mutation carriers were classified as sporadic cases. The ages of onset in these patients were 58, 70 and 82 years. The presence of the nonsense mutation in all patients with Parkinson was confirmed by automated capillary sequencing (CEQ 2000 system, Beckman Coulter Inc., Fullerton, Calif.). Frequencies of the SNP were determined by pyrosequencing.

Mutation Screening:

Stockholm Material:

Venous blood samples were drawn and genomic DNA isolated from 123 consecutive outpatients (72 male and 51 female, average age 69 years and age of onset 61 years) with idiopathic PD according to the "brain bank clinical diagnostic criteria for Parkinson's disease" (Daniel S E, Lees A J. Parkinson's Disease Society Brain Bank, London: overview and research. J Neural Transm Suppl 1993;39:165-172) with the exception that presence of relatives with PD was not an exclusion criterion. All patients were informed about the aim of the study and the study was approved by the Swedish ethical committee (filed under Dnr. 96-377). Twenty-nine percent of patients reported family history of PD in one or more first-, second-or third-degree relatives. An additional eleven percent of cases had relatives with more uncertain types of "tremor." 127 controls were geographically matched healthy, unrelated individuals (50% male, 50% female, average age 39 years).

Pyrosequencing:

In the PCR reaction for the pyrosequencing fragment, one of the primers, the reverse primer

TCCTGTACCTGGTTTGACTG SEQ ID NO. 3 was biotinylated to allow subsequent immobilization to streptavidin coated beads. The forward primer was:

CTGTGATTTTAGGCCATGAG SEQ ID NO. 4

AmpliTaq Gold DNA polymerase (PE Biosystems) was used for the PCR reaction. The magnesium concentration was 2.5 mM for this fragment. Forty-five cycles were run at 95° C. for 20 seconds, 57° C. for 20 seconds and 72° C. for 30 seconds. After PCR the biotinylated PCR product was immobilized onto Streptavidin-coated Dynabeads (Dynal Biotech, Oslo, Norway). The DNA template and beads were mixed continuously for 20 min at 65° C. The immobilized DNA template was then transferred to a PSQ™ 96 Plate. After two minutes in denaturation solution, the beads were rinsed twice in wash buffer and the single-stranded template was annealed to the sequencing primer (in opposite direction to the biotinylated primer):

ATCGTGGAAAGTGTT SEQ ID NO. 5

The annealing reaction was performed in annealing buffer at 90° C. for two minutes and cooled to room temperature. All solutions used in sample preparation were from the PSQ™ 96 Sample Preparation Kit (Pyrosequencing AB, Uppsala, Sweden). Samples were analyzed on an automated pyrosequencer using a PSQ 96 System together with SNP Software and SNP Reagent Kits (Pyrosequencing AB, Uppsala, Sweden) applying the following nucleotide dispension order: CGTGCAG (yielding a better resolution for the extra signal caused by the T nucleotide in the mutant sequence than the first tried dispension order CTGCAGA). Standard instructions were followed.

TABLE I

Comparisons of distributions of allele frequencies of the ADH1C mutation between PD patients and controls.

| SNP | Controls | | | Parkinson's Disease | | | P-value* |
|---|---|---|---|---|---|---|---|
| ADH1C | N | wt (%) | mt (%) | N | wt (%) | mt (%) | |
| nonsense | 127 | 100 | 0 | 123 | 98.8 | 1.2 | 0.19 |

N: Number of individuals;
wt: wildtype residue G;
mt: mutated residue T;
*Chi-square test with Yates' correction.

Automated Capillary Sequencing:

Polymerase chain reaction (PCR) was carried out using Taq DNA polymerase (SIGMA, St. Louis, Mo.) using the following primers:

```
forward primer
TTTTAGAAAATTGGGTTTGTTAAGTC      SEQ ID NO. 6 reverse primer
CCTTGTGCAAGTCCTTTCGTC           SEQ ID NO. 7
```

The fragment was amplified for 35 cycles at 94° C. for 40 seconds, 56° C. for 45 seconds and 72° C. for one minute. After PCR, the samples underwent electrophoresis on 1% low-melting agarose gels and visualized using UV-transillumination after ethidium bromide staining. DNA was extracted from gel slices (PCR preps DNA purification kit, SDS, Falkenberg, Sweden) and DNA fragments were sequenced using a DTCS kit followed by automated capillary gel electrophoresis (CEQ 2000 system, Beckman Coulter Inc., Fullerton, Calif.).

17 more Swedish PD patients and 3 more controls (Stockholm material) and an American, German, English and another Swedish material (see Table II) were investigated using pyrosequencing. We found the nonsense mutation in: 6 of 130 PD patients from Department of Neurology, Baylor College of Medicine, Houston, Tex., USA, none of 100 matched controls from that region, 1 of 110 PD patients from GEPARD consortium Department of Neurology, University of Bonn, Bonn, Germany, none of their 30 matched controls, 2 of 119 PD patients from Queen Square Brain Bank for Neurological Disorders, Institutete of Neurology, London, England, none of 78 matched controls and none of 105 PD patients from Department of Pharmacology, Göteborg University, Gothenburg, Sweden and none of 180 controls. All cases where the nonsense mutation was observed by pyrosequencing were confirmed by capillary sequencing.

TABLE II

Individuals with the G78stop mutation.

| Area | Groups | N | G78stop |
|---|---|---|---|
| Stockholm, Sweden | PD | 140 | 3 |
| | Controls | 130 | 0 |
| Baylor, USA | PD | 130 | 6 |
| | Controls | 100 | 0 |
| Bonn, Germany | PD | 110 | 1 |
| | Controls | 30 | 0 |
| London, England | PD | 119 | 2 |
| | Controls | 78 | 0 |
| Gothenburg, Sweden | PD | 105 | 0 |
| | Controls | 180 | 0 |

All these findings indicate a significant association of this mutation with PD using Chi-square test with Yates' correction (p = 0.0004).

Since these patients are undistinguishable from other idiopathic PD cases, the identification of the ADH1C nonsense mutation in these individuals may lead to new disease pathway in the most common, idiopathic type of PD. In contrast to other identified mutations, ADH1C constitutes a clear link to "outside" factors, such as environmental toxins or alike. Thus, our results suggest that there is an association of the ADH1C mutation with Parkinson's disease.

The invention claimed is:

1. A method for indentifying a person at increased risk for developing Parkinson's disease, comprising screening nuleic acids from said person for a mutation in an ADH1C gene which encodes a protein chain, said mutation causing a truncation of the expressed protein chain,
wherein the ADH1C gene is selected from the group consisting of a gene having a cDNA sequence of SEQ ID NO. 1 and other ADH1C genes having a thymidine at or corresponding to position 303 in SEQ ID NO. 1.

2. The method according to claim 1, wherein the screening comprises at least one procedure selected from the group consisting of DGGE, SSCP, HA, temperature gradient gel electrophoresis TGGE, cleavage-fragment-length polymorphism analysis CFLP, dHPLC, CCM, CDI, ECM, UNG-mediated T Scan, direct sequencing, DNA chip resequencing, Pyrosequencing™, allele-specific primer extension (GBA; TDI), oligonucleotide ligation assay (OLA; DOL), Taqman-ASO, RFLP, mass spectrometry, the Invader™ assay, BeadArray™ technology, or any equivalent procedure which detects the mutation.

3. The method according to claim 1, which the screening comprises at least one procedure selected from the group considering of direct sequencing, Pyrosequencing™, Taqman-ASO to specifically detect the mutation.

4. The method according to claim 1, wherein the screening comprises restriction enzymes specifically recognizing a nucleotide sequence of the mutation or surrounding the mutation to be detected.

5. The method according to claim 1, wherein the screening comprises hybridising under stringent condition an oligonucleotide to the ADH1C gene comprising the mutation.

* * * * *

SEQUENCE LISTING

<160> NUMBER OF SEQ ID NOS: 7

<210> SEQ ID NO 1
<211> LENGTH: 1470
<212> TYPE: DNA
<213> ORGANISM: Homo sapiens
<220> FEATURE:
<221> NAME/KEY: gene
<222> LOCATION: (1)..(1470)
<223> OTHER INFORMATION: ADH1C sequence with mutation at position 303

<400> SEQUENCE: 1

```
atgcactcaa gcagagaaga aatccacaag tactcaccag cctcctggtc tgcagagaag      60
acagaatcaa tatgagcaca gcaggaaaag taatcaaatg caaagcagct gtgctatggg     120
agttaaagaa acccttttcc attgaggagg tagaggttgc acctcctaag gctcatgaag     180
ttcgcattaa gatggtggct gcaggaatct gtcgttcaga tgagcatgtg gttagtggca     240
acctggtgac cccccttcct gtgattttag gccatgaggc agccggcatc gtggaaagtg     300
tttgagaagg ggtgactaca gtcaaaccag gtgataaagt catcccgctc tttactcctc     360
agtgtggaaa atgcagaatt tgtaaaaacc cagaaagcaa ctactgcttg aaaaatgatc     420
taggcaatcc tcgggggacc ctgcaggatg gcaccaggag gttcacctgc agcgggaagc     480
ccatccacca cttcgtcggc gtcagcacct tctcccagta cacagtggtg gatgagaatg     540
cagtggccaa aattgatgca gcctcgcccc tggagaaagt ctgcctcatt ggctgtggat     600
tttcgactgg ttatgggtct gcagtcaaag ttgccaaggt caccccaggg tctacctgtg     660
ctgtgtttgg cctgggaggg gtcggcctat ctgttgttat gggctgtaaa gcagctggag     720
cagccagaat cattgctgtg gacatcaaca aggacaaatt tgcaaaggct aaagagttgg     780
gggccactga atgcatcaac cctcaagact acaagaaacc cattcaggaa gtgctaaagg     840
aaatgactga tggaggtgtg gattttcgt ttgaagtcat cggtcggctt gacaccatga     900
tggcttccct gttatgttgt catgaggcat gtggcacaag tgtcattgta ggggtacctc     960
ctgattccca gaacctctca ataaacccta tgctgctact gactggacgc acgtggaaag    1020
gagctatttt tggaggcttt aagagtaaag aatctgtccc gaaacttgtg gctgacttta    1080
tggctaagaa gttttcactg gatgcattaa taacaaatat tttaccttttt gaaaaaataa    1140 atgaaggatt tgacctgctt cgctctggaa agagtatccg taccgtcctg acgttttgaa    1200
acaatacaga tgccttccct tgtagcagtt ttcagcctcc tctaccctac atgatctgga    1260
gcaacagcta ggaaatatca ttaattctgc tcttcagaga tgttaaaaat aaattacacg    1320
tgggagcttt ccaaagaaat ggaaattgat gggaaattat ttgtcaagca aatgtttaaa    1380
atccaaatga gaactaaata aagtgttgaa catcaactgg ggaattgaag ccaataaacc    1440
ttccttctta accattcaaa aaaaaaaaaa                                     1470
```

<210> SEQ ID NO 2
<211> LENGTH: 1470
<212> TYPE: DNA
<213> ORGANISM: Homo sapiens
<220> FEATURE:
<221> NAME/KEY: gene

```
<222> LOCATION: (1)..(1470)
<223> OTHER INFORMATION: ADH1C wildtype sequence

<400> SEQUENCE: 2
atgcactcaa gcagagaaga aatccacaag tactcaccag cctcctggtc tgcagagaag      60
acagaatcaa tatgagcaca gcaggaaaag taatcaaatg caaagcagct gtgctatggg     120
agttaaagaa acccttttcc attgaggagg tagaggttgc acctcctaag gctcatgaag     180
ttcgcattaa gatggtggct gcaggaatct gtcgttcaga tgagcatgtg gttagtggca     240
acctggtgac ccccttcct gtgattttag gccatgaggc agccggcatc gtggaaagtg      300
ttggagaagg ggtgactaca gtcaaaccag gtgataaagt catcccgctc tttactcctc     360
agtgtggaaa atgcagaatt tgtaaaaacc cagaaagcaa ctactgcttg aaaaatgatc     420
taggcaatcc tcgggggacc ctgcaggatg gcaccaggag gttcacctgc agcgggaagc     480
ccatccacca cttcgtcggc gtcagcacct tctcccagta cacagtggtg gatgagaatg     540
cagtggccaa aattgatgca gcctcgcccc tggagaaagt ctgcctcatt ggctgtggat     600
tttcgactgg ttatgggtct gcagtcaaag ttgccaaggt caccccaggg tctacctgtg     660
ctgtgtttgg cctgggaggg gtcggcctat ctgttgttat gggctgtaaa gcagctggag     720
cagccagaat cattgctgtg gacatcaaca ggacaaatt tgcaaaggct aaagagttgg      780
gggccactga atgcatcaac cctcaagact acaagaaacc cattcaggaa gtgctaaagg     840
aaatgactga tggaggtgtg gattttcgt tgaagtcat cggtcggctt gacaccatga       900
tggcttccct gttatgttgt catgaggcat gtggcacaag tgtcattgta ggggtaccta     960
ctgattccca gaacctctca ataaacccta tgctgctact gactggacgc acgtggaaag    1020
gagctatttt tggaggcttt aagagtaaag aatctgtccc gaaacttgtg gctgacttta    1080
tggctaagaa gttttcactg gatgcattaa taacaaatat tttacctttt gaaaaaataa    1140
atgaaggatt tgacctgctt cgctctggaa agagtatccg taccgtcctg acgttttgaa    1200
acaatacaga tgccttccct tgtagcagtt ttcagcctcc tctaccctac atgatctgga    1260
gcaacagcta ggaaatatca ttaattctgc tcttcagaga tgttaaaaat aaattacacg    1320
tgggagcttt ccaaagaaat ggaaattgat gggaaattat tgtcaagca aatgtttaaa     1380 atccaaatga aactaaaata agtgttgaa catcaactgg ggaattgaag ccaataaacc      1440
ttccttctta accattcaaa aaaaaaaaa                                       1470

<210> SEQ ID NO 3
<211> LENGTH: 20
<212> TYPE: DNA
<213> ORGANISM: Artificial
<220> FEATURE:
<221> NAME/KEY: misc_feature
<222> LOCATION: (1)..(20)
<223> OTHER INFORMATION: reverse primer

<400> SEQUENCE: 3
tcctgtacct ggtttgactg                                                   20

<210> SEQ ID NO 4
<211> LENGTH: 20
<212> TYPE: DNA
<213> ORGANISM: Artificial
<220> FEATURE:
<221> NAME/KEY: misc_feature
<222> LOCATION: (1)..(20)
<223> OTHER INFORMATION: forward primer
```

-continued

```
<400> SEQUENCE: 4
ctgtgatttt aggccatgag                                                     20

<210> SEQ ID NO 5
<211> LENGTH: 15
<212> TYPE: DNA
<213> ORGANISM: Artificial
<220> FEATURE:
<221> NAME/KEY: misc_feature
<222> LOCATION: (1)..(15)
<223> OTHER INFORMATION: sequencing primer

<400> SEQUENCE: 5
atcgtggaaa gtgtt                                                          15

<210> SEQ ID NO 6
<211> LENGTH: 26
<212> TYPE: DNA
<213> ORGANISM: Artificial
<220> FEATURE:
<221> NAME/KEY: misc_feature
<222> LOCATION: (1)..(26)
<223> OTHER INFORMATION: forward primer

<400> SEQUENCE: 6
ttttagaaaa ttgggtttgt taagtc                                              26

<210> SEQ ID NO 7
<211> LENGTH: 21
<212> TYPE: DNA
<213> ORGANISM: Artificial
<220> FEATURE:
<221> NAME/KEY: misc_feature
<222> LOCATION: (1)..(21)
<223> OTHER INFORMATION: reverse primer

<400> SEQUENCE: 7
ccttgtgcaa gtcctttcgt c                                                   21
```